United States Patent
Comparat et al.

(10) Patent No.: US 11,570,972 B2
(45) Date of Patent: Feb. 7, 2023

(54) PROCESS FOR REARING INSECTS

(71) Applicant: YNSECT, Evry (FR)

(72) Inventors: Solène Comparat, Evry (FR); Antoine Hubert, Alfortville (FR); Fabrice Berro, Paris (FR); Jean-Gabriel Levon, Paris (FR)

(73) Assignee: YNSECT, Évry-Courcouronnes (FR)

( * ) Notice: Subject to any disclaimer, the term of this patent is extended or adjusted under 35 U.S.C. 154(b) by 896 days.

(21) Appl. No.: 15/565,691

(22) PCT Filed: Apr. 12, 2016

(86) PCT No.: PCT/FR2016/050843
§ 371 (c)(1),
(2) Date: Oct. 11, 2017

(87) PCT Pub. No.: WO2016/166465
PCT Pub. Date: Oct. 20, 2016

(65) Prior Publication Data
US 2018/0077912 A1  Mar. 22, 2018

(30) Foreign Application Priority Data
Apr. 13, 2015 (FR) ...................... 1553208

(51) Int. Cl.
*A01K 67/033* (2006.01)
(52) U.S. Cl.
CPC .................. *A01K 67/033* (2013.01)
(58) Field of Classification Search
CPC .. A01K 67/00; A01K 67/033; A01K 67/0332; A01K 1/0047; A01K 29/00;
(Continued)

(56) References Cited

U.S. PATENT DOCUMENTS 2,539,633 A * 1/1951 Morrill ................ A01K 67/033
119/6.5
3,654,903 A * 4/1972 Montgomery .......... C05F 17/05
47/17
(Continued)

FOREIGN PATENT DOCUMENTS

KR 2003032253 A * 4/2003 ......... A01K 67/0332
UA 20040907862 12/2006
(Continued)

OTHER PUBLICATIONS

International Search Report dated Jul. 1, 2016, in corresponding PCT Application No. PCT/FR2016/050843.
(Continued)

*Primary Examiner* — Ebony E Evans
(74) *Attorney, Agent, or Firm* — Panitch Schwarze Belisario & Nadel LLP; Erin M. Dunston (57) ABSTRACT

The invention relates to a method for breeding insects, comprising growth phases during which the insects are stored in a controlled environment, said growth phases alternating with operating sequences during which at least one specific breeding operation is performed. The method comprises a sequence, referred to as synchronization sequence, during which a batch of insects is sorted and divided into a plurality of size or maturity categories in separate containers, then said containers (31, 32) are grouped together to form basic breeding units (UE) comprising a predefined number of containers (31, 32), a basic breeding unit (UE) comprising only insects of the same category.

25 Claims, 4 Drawing Sheets

(58) Field of Classification Search
CPC ........ A01K 29/005; A01K 5/00; A01K 97/04; A01K 2227/706
USPC ............... 119/6.6, 6.7, 300, 322, 635, 651
See application file for complete search history.

(56) References Cited

U.S. PATENT DOCUMENTS

| | | | | |
|---|---|---|---|---|
| 4,411,220 | A * | 10/1983 | Voegele | A01K 67/033 119/6.6 |
| 4,765,274 | A * | 8/1988 | Pizzol | A01K 67/033 119/6.6 |
| 4,850,305 | A * | 7/1989 | Georgi | A01K 67/033 119/6.6 |
| 5,351,643 | A * | 10/1994 | Hughes | A01K 67/033 119/6.5 |
| 6,474,259 | B1 * | 11/2002 | Gaugler | A01K 67/033 119/6.7 |
| 7,429,398 | B1 * | 9/2008 | Sipe | A01K 97/04 426/520 |
| 8,025,027 | B1 * | 9/2011 | Morales-Ramos | A01K 67/033 119/6.5 |
| 9,462,795 | B2 * | 10/2016 | Chin | A01K 67/033 |
| 9,629,339 | B2 * | 4/2017 | Newton | A01K 67/033 |
| 10,159,229 | B2 * | 12/2018 | Marchant | A01K 67/033 |
| 10,306,875 | B1 * | 6/2019 | Massaro | A01K 67/033 |
| 2003/0188698 | A1 * | 10/2003 | Donaldson | A01K 67/033 119/678 |
| 2003/0233982 | A1 * | 12/2003 | Zhang | A01K 67/033 119/6.5 |
| 2009/0012186 | A1 * | 1/2009 | Bolckmans | A01K 67/033 514/789 |
| 2011/0081452 | A1 * | 4/2011 | Hem | A23K 50/80 119/6.6 |
| 2011/0174222 | A1 * | 7/2011 | Lee | A01K 67/033 119/6.6 |
| 2011/0236319 | A1 * | 9/2011 | Binning | A01N 25/00 424/9.2 |
| 2011/0238207 | A1 * | 9/2011 | Bastian, II | B65G 61/00 700/217 |
| 2014/0020630 | A1 * | 1/2014 | Courtright | A01K 67/033 119/6.6 |
| 2015/0008163 | A1 * | 1/2015 | Nimmo | B07B 13/04 209/17 |
| 2018/0070566 | A1 * | 3/2018 | Comparat | B65G 1/0407 |
| 2018/0092339 | A1 * | 4/2018 | Massaro | A01K 67/033 |
| 2018/0103679 | A1 * | 4/2018 | Leo | A01K 67/033 |

FOREIGN PATENT DOCUMENTS

| | | |
|---|---|---|
| UA | 54655 U | 11/2010 |
| WO | WO 2014/171829 | 10/2014 |

OTHER PUBLICATIONS

Office Action (Preliminary Examination Report) dated Nov. 15, 2019, by the Ukrainian Institute of Intellectual Property State-Owned Enterprise in corresponding Ukrainian Patent Application No. a 2017 10083 and an English Translation of the Office Action. (22 pages).

* cited by examiner

PROCESS FOR REARING INSECTS

CROSS-REFERENCE TO RELATED APPLICATIONS

This application is a U.S. National Stage Application pursuant to 35 U.S.C. § 371 of International Patent Application PCT/FR2016/050843, filed on Apr. 12, 2016, and published as WO 2016/166465 on Oct. 20, 2016, which claims priority to French Patent Application 1553208, filed on Apr. 13, 2015, all of which are incorporated herein by reference in their entireties for all purposes.

The present invention relates to the field of rearing insects. In particular, it relates to a process for rearing insects.

Insects, in particular certain species, can constitute a source of products or of raw materials, in particular for animal or human foodstuffs, or for use by many other industries.

Unless otherwise stated, by the term "insect" used in the present document is meant any stage of development from the egg or egg sac to the adult insect, passing through the larva and the nymph or pupa.

In particular, by the term "larva" is meant in the present document the larval stage of the insects, which includes the maggot stage for Diptera and the caterpillar stage for Lepidoptera, as well as the wingless stages in Orthoptera. By the term "nymph" is meant in the present document the intermediate stages between the larva and the imago, which includes the pupa for Diptera, the nymph for Coleoptera, the chrysalis for Lepidoptera and, if applicable, an intermediate stage during which certain physiological (prepupa) or behavioural modifications of the individuals appear, such as a significant sclerification of the cuticle for Diptera. Similarly, the term "egg" also covers an egg sac of Dictyoptera.

Typically, certain species of edible insects are rich in proteins. Approximately two thousand species of edible insects have been identified to date, and this number is increasing regularly. Many insects can be used for fodder for rearing farm animals (mammals, birds, etc.), farmed fish and aquatic invertebrates, etc. In general, insects convert a large proportion of what they ingest into body mass (in particular markedly more than mammals do). In fact, their metabolism is that of poikilothermic organisms, which do not need to use energy in order to maintain their body temperature. On the other hand, the higher animals, called homeotherms, use significant energy in order to maintain their body temperature. The domestication of insects for the purposes of feed production thus constitutes an opportunity with regard to the worldwide challenges in respect of nutrition and protection of the environment.

Apart from the food aspect, insects can constitute a significant resource in many industrial fields. Typically, the exoskeleton of insects is constituted in large part by chitin, a known derivative of which is chitosan. The applications of chitin and/or chitosan are many: cosmetics (cosmetic composition), medical and pharmaceutical (pharmaceutical composition, treatment of burns, biomaterials, corneal dressings, surgical sutures), dietetic and dietary, technical (filtering, texturing agent, flocculating agent or adsorbant, in particular for water filtration or pollution control), etc. In fact, chitin and chitosan are biocompatible, biodegradable and non-toxic materials.

Insect rearing has thus experienced some rapid growth. Certain methods and devices relating to such rearing have thus been developed. A process and an associated device are known for example from document WO2014/171829 making it possible to automate the supply of food in insect rearing crates. More specifically, this document discloses a device making it possible to determine, by a process of observation of each of the crates of a farm, the condition and stage of growth of the insects present in each of the crates, and if a supply of food is required in the crate in question.

Thus, although certain known processes solve certain problems of simplification in an insect farm, no known process is particularly suitable for insect rearing on a large scale.

In particular, optimizing the productivity of large-scale rearing remains a problem that is poorly understood or solved in an unsatisfactory manner in the state of the art. Now, large-scale rearing would make it possible to obtain sufficient quantities of products in order to interest the food commodities and chemical markets in particular.

The purpose of the present invention is to overcome at least one of the aforementioned drawbacks. The present invention relates in particular to proposing a device, in particular a farm, optimizing the logistics associated with insect rearing, and generally, carrying out rearing over a complete cycle of insect production.

In particular, the invention relates to a process for insect rearing comprising growth phases during which the insects are stored in a controlled environment, said growth phases alternating with operational sequences during which at least one specific rearing operation is carried out. The process that is the subject of the invention comprises a sequence called a synchronization sequence during which a batch of insects is sorted and distributed into several categories of size or maturity in different containers, then said containers are grouped together in order to constitute basic rearing units comprising a predefined number of containers, one basic unit comprising only insects of the same category.

Such a process, made possible by the large scale of the farm in which it is applied, allowing significant batches of insects at the same stage of development or of the same maturity to be constituted, makes it possible to sequence the rearing operations to be applied synchronously over a basic rearing unit or several basic rearing units.

The sequences of rearing operations, i.e. the sets of operations to be performed, can be predetermined and carried out without any other monitoring than for time, or relying on simple specific controls of the growth of the insects at predetermined times.

The process is thereby optimized and can easily be automated, compared for example with traditional rearing in individual compartments in which each compartment must be managed and sorted individually. If necessary, grouping the containers in basic units (typically palletized) allows optimized industrial management of rearing at different levels: by container, by basic rearing unit, by batches of basic units.

The rearing and control operations can be carried out in an automated manner, and their implementation rationalized. Automating the operations makes it possible to increase the robustness of the process and the quality of the final product and to avoid all human error. This also makes it possible to collect more data relating to rearing, more quickly, using sensors (capable in particular of operating continuously) and the automation of all or part of the operations.

Harvesting the final product(s) of rearing (adult insects of a given maturity, larvae, etc.) is carried out per basic unit. Due to the synchronization of the insects during rearing, the harvested insects in each basic unit have good homogeneity. In particular, during harvesting of the insects with a view to sending them to a reuse process, the level of unwanted elements (for example insects not of the required grade, dead insects, droppings) is low.

Thus, the formation of basic rearing units, comprising insects at the same stage of development, allows simple sequential management of the rearing process implemented in the farm. Thus, management of industrial type production heretofore unknown in the field of insect rearing can be utilized with, typically, complete automation of all of the handling, feeding, control and observation operations on the basic units.

According to a variant of the invention, the synchronization sequence can be conducted several times on each insect during said process.

According to an embodiment, the process can comprise a sequence called concentration/dilution of the insects, in which the density of insects in each container of a rearing unit is brought to a target density by the addition of insects, the removal of insects, or the distribution of the insects in the containers, the target density corresponding to a desired predetermined density at the start of the subsequent storage phase.

The target density can correspond to the density for which it is estimated that, taking account of the expected growth of the insects during the subsequent storage phase, the desired time interval separating the current concentration/dilution sequence from a following concentration/dilution sequence will end with a density considered maximal ensuring good health of the insects in the containers.

The target density can alternatively be defined by a ratio of the density in the containers before the concentration/dilution sequence.

The density of insects can also in particular be either:
a weight of insects by volume or by surface area of the container; or
a number of insects by volume or by surface area of the container.

According to an embodiment, the process can combine:
a process called production process, for insect rearing, from the egg or from the juvenile stage up to the larval stage with a predefined maturity; or
a process called reproduction process, for insect rearing from the egg or from the juvenile stage up to the young adult stage, associated with a process called egg-laying process, relating to the production of eggs or juveniles by adult insects.

The process can comprise, between each growth phase, a step of automated transport of the basic rearing units containing the insects that are to be the subject of at least one operating sequence, from a storage zone in which said growth phase takes place, to an operating zone comprising work stations suitable for rearing operations of the operating sequence.

The process can comprise operating sequences for feeding.

The process can comprise operating sequences for providing water.

The process can comprise an operating sequence for withdrawal of adult insects intended for egg laying.

The process can comprise the following operating sequences:
collecting eggs from the rearing containers containing insects intended for egg-laying,
concentrating eggs in rearing containers.

The process can comprise the following operating sequences:
collecting juveniles from the rearing containers (31, 32) containing insects intended for egg-laying,
concentrating juveniles in rearing containers (31, 32).

The process can comprise an operating sequence of emptying and cleaning rearing containers for the reuse thereof.

The operating sequences can comprise the ordered succession of several operations among the following operations:
Storing a basic rearing unit in a controlled environment;
Removing a basic rearing unit from storage:
Partially or totally degrouping the rearing containers from a basic rearing unit;
Grouping together rearing containers into a basic rearing unit;
Depositing rearing substrate in a rearing container;
Providing water in a rearing container;
Emptying a rearing container;
Identifying the individuals having symptoms of disease in order to remove them from the container.
Separating the fine waste, comprising the droppings, the remains of the substrate and the molts, from the insects;
Separating the mature live larvae and the substrate that has not been consumed;
Separating the dead larvae from the live larvae;
Grading the larvae according to their size;
Sorting the adult insects from the larvae and the nymphs;
Sorting the live insects from the dead insects;
Sorting the eggs from the adults and sorting the eggs from the substrate;
Sorting the nymphs from the larvae;
Cleaning a rearing container;
Filling a rearing container with insects;
Taking a rearing unit from rearing and sending it to another process;
Introducing a new rearing unit;
Throwing away the contents of a rearing container.

In particular, the synchronization sequence can be carried out at the larval stage by implementation of a sequence of grading of the larvae comprising the following operations:
Removing a basic rearing unit from storage:
Partially or totally degrouping the rearing containers from a basic rearing unit;
Emptying the rearing containers;
Cleaning the rearing containers;
Separating the droppings and the live larvae;
Grading the larvae according to their size;
Filling the rearing containers with the live larvae;
Depositing rearing substrate in the rearing containers;
Grouping together the rearing containers into a basic rearing unit;
Storing the basic rearing units in a controlled environment;

In particular, the concentration/dilution sequence can comprise the following operations:
Removing a basic rearing unit from storage:
Totally degrouping the rearing containers from the basic rearing unit;
Emptying the rearing containers;
Cleaning the containers;
Separating the droppings and the live larvae;
Filling rearing containers with insects, to the desired density;
Depositing rearing substrate;
Grouping together the rearing containers into basic rearing units;

Storing the basic rearing units in a controlled environment; The synchronization sequence and the concentration/dilution sequence can also comprise an operation for providing water.

Other features and advantages of the invention will become more apparent from the following description.

Figure 1:
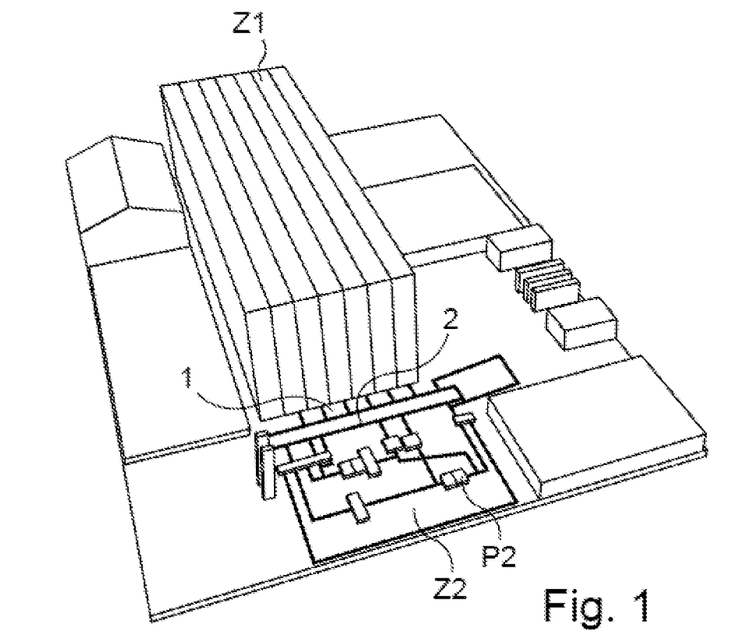
FIG. 1 shows, in a diagrammatic three-dimensional view, an example of a farm allowing the implementation of a process according to an embodiment of the invention.

In the attached drawings, given non-limitatively by way of example:

FIG. 1 shows a farm for rearing insects, shown here in the form of three-dimensional diagrammatic view, particularly suitable for the implementation of a preferential variant of the process that is the subject of the invention.

The farm shown comprises at least two zones, namely a first zone Z1 organized for the storage of the insects during their growth, i.e. during the growth phases of the process that is the subject of the invention. In this first zone Z1, the insects increase in size under controlled, supervised and optimized environmental conditions (defined by environmental parameters including temperature, hygrometry, etc.).

As previously mentioned, the concept of insect rearing comprises the growth of adult insects up to a desired stage, but can also comprise all the phases that precede obtaining an adult insect (or imago), from the laying of eggs (or egg sacs), passing through their hatching, the larval stage, any nymph or pupal stage, (the set of intermediate stages), etc.

In a variant of the process that is the subject of the invention, insect rearing can in particular be envisaged as an organized whole allowing the laying of eggs by adult insects for the production of larvae, some larvae being reared to the adult stage for laying new eggs, the adults being regularly renewed (for example following their death) by young adults providing new egg laying and so on. The final products of the production can be eggs, and/or larvae, and/or nymphs, and/or adult insects.

The farm shown here also comprises a second zone Z2, organized for carrying out one or more rearing operations or sequences. Conducting the rearing comprises the implementation of a succession of rearing sequences or operations. A sequence or "operating sequence" comprises one or more predefined successive operations and is carried out between two growth phases (except when the insects are to be sent to another process).

The rearing operations correspond to operations that must be conducted in order to maintain life, good growth and/or the optimization of the insect rearing conditions.

The second zone Z2 comprises in particular one or more specialized work stations P1, P2 for carrying out one or more rearing operations. In particular, the second zone Z2 can be adapted in order to allow the implementation, at one or more work stations, of rearing sequences constituted by a succession of single operations. The work stations can typically be grouped together in islands for the implementation of successive operations. Stations P1, P2 or islands of stations can be served by a belt conveyor 2.

The insects (eggs, larvae, nymphs, or adults) are reared in containers grouped into basic rearing units, preferably in the form of pallets. During growth phases, the palettes are stored in the first zone Z1, for example in pallet racks.

In order to conduct rearing operations that are identical for all the containers and all the insects of one and the same basic rearing unit, a sequence called synchronization sequence can be implemented in the process, a sequence during which a batch of insects is sorted so as to distribute the insects (eggs, larvae, nymphs, pupae, adults, etc.) by size or maturity into different containers, then grouping together the containers in order to constitute basic rearing units comprising a predetermined number of containers. In particular, the containers are grouped together so that one and the same basic unit contains insects that are substantially at the same stage of development or of the same maturity. In a basic unit constituted during the synchronization sequence, according to the accuracy of the sorting or grading performed, typically at least 80% of insects have substantially the same maturity, and preferentially at least 90% of insects have the same maturity.

The synchronization can typically be carried out shortly after the laying of eggs or egg sacs, so that a basic rearing unit at the start of the rearing cycle contains only eggs laid within an interval of a few days at most. A synchronization sequence can be provided several times between the laying of an egg and obtaining the final product of rearing, and/or between the laying of an egg and obtaining an adult insect. Typically, the synchronization can be carried out by implementing a grading sequence, for example by size, at the larval stage.

For carrying out certain operations, in particular sorting or grading operations during a synchronization sequence, it may prove necessary to depalletize or degroup the rearing containers. According to various possible modes of organization, this operation can be carried out at the level of an interface 1, or on a dedicated station of the second zone Z2.

Figure 2:
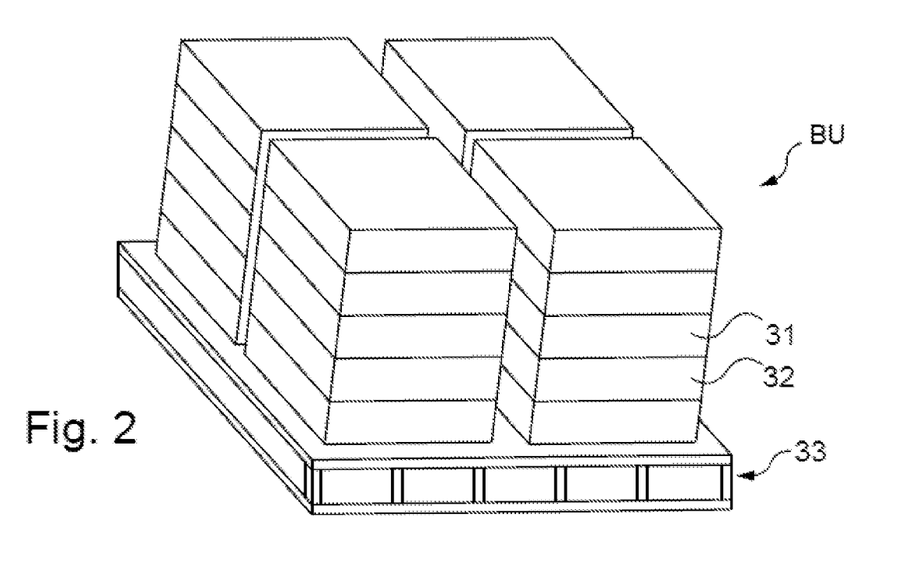
FIG. 2 shows, in a diagrammatic view, a basic unit for insect rearing.

In the invention, the growth of the insects, i.e. the rearing phases outside of the specific rearing operations, takes place in basic rearing units that have undergone a synchronization sequence. Merely by way of example, FIG. 2 shows an example of a basic rearing unit BU, according to a three-dimensional schematic diagram. In particular, the rearing containers 31, 32 can be stackable crates or compartments. By stackable crates or compartments is meant in particular crates or compartments that are superimposed on one another in a slightly embedded manner, which achieves a certain stability for the column of crates thus formed.

As shown in FIG. 2, the containers 31, 32 are palletized, i.e. grouped as basic units BU on a loading pallet 33. The pallet 33 can in particular, but not exclusively, be a pallet of a standard size, i.e. typically a pallet of the "Euro pallet" type or a half-pallet of this type.

By way of example, a basic rearing unit BU can typically group together from eight to one hundred containers, and comprise one, two, three or four stacks of containers or even more. The height of a complete basic rearing unit can for example comprise between 160 and 230 cm, and typically of the order of 200 cm.

During the phases called growth phases, each basic unit can be stored in a part or silo of the first zone Z1 having optimized environmental conditions for the stage of development (or maturity) of the insects of the basic unit in question.

The silos are isolated from one another by suitable partitioning. This partitioning of silos can utilize air curtains, or any other partitioning means making it possible to separate two zones in order to be able to ensure therein two different atmospheric conditions (temperature, hygrometry, etc.) and sanitary separation between the silos. For example, physical partitions can be utilized. The first zone Z1 can comprise several different stores, separated by physical partitions.

The silos thus constituted can be dedicated to different stages of maturity of the insects, or to several rearing processes, according to embodiments of the invention and conducted in parallel in one rearing.

For example, conducting the rearing can comprise several cycles, with which different rearing conditions can be associated. Typically, the rearing can comprise:
- an incubation cycle for the production of juveniles by fertile adults, this cycle being conducted at a temperature and under conditions of humidity that are relatively high;
- a reproduction cycle, from the juvenile to the young mature fertile adult, passing through nymphosis, under suitable environmental conditions;
- a cycle of production (or "finishing") from the juvenile to the mature larva for killing, with lower temperature and humidity.

Figure 3:
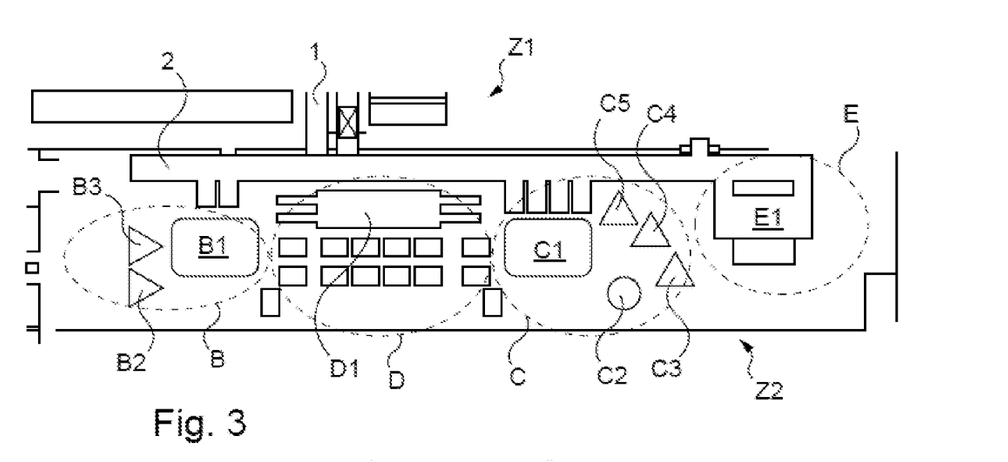
FIG. 3 shows, in a diagrammatic view, an example of the organization of a second zone of a farm allowing the implementation of a process according to an embodiment of the invention.

FIG. 3 shows, in a diagrammatic view, an example of the organization of a second zone Z2 of a farm suitable for the implementation of a process according to an embodiment of the invention.

The example of a second zone Z2 shown in FIG. 3 is represented within the context of the example farm in FIG. 1. In particular, FIG. 3 shows the interface 1 with the first zone Z1. A conveyor system, namely in the example shown a belt conveyor, 2 ensures the movement of the basic units or if applicable, the degrouped containers. A storage/retrieval machine, after selecting a pallet from the first zone Z1, places the latter at the entry to the conveyor system, namely typically on a zone of the belt conveyor 2 forming an interface 1 between the first zone Z1 and the second zone Z2, or any other device allowing the pallet to be sent to said belt conveyor 2 at the time desired. In the example shown here, the palletized basic units are directed by the belt conveyor 2 to the depalletization (and palletization) zones, in this case a first logistics zone B1 and a second logistics zone B2.

Generally, the example second zone Z2 shown here is organized in four sub-zones called islands, referenced respectively B, C, D and E. The islands B, C, D and E are associated with one or more rearing operations, for which they are more or less specialized.

Generally, carrying out the operating sequences implemented in the invention can comprise one or more of the following main rearing operations (and if applicable, other additional operations):
- Storing a basic rearing unit in a controlled environment;
- Removing a basic rearing unit from storage;
- Partially or totally degrouping the rearing containers from a basic rearing unit;
- Grouping together rearing containers into a basic unit;
- Depositing rearing substrate in a rearing container;
- Providing water in a rearing container;
- Emptying a rearing container;
- Identifying the individuals having symptoms of disease in order to remove them from the container.
- Separating the fine waste, comprising the droppings, the remains of the substrate and the molts, from the insects;
- Separating the mature live larvae and the substrate that has not been consumed;
- Separating the dead larvae from the live larvae;
- Grading the larvae according to their size;
- Sorting the adult insects from the larvae and the nymphs;
- Sorting the live insects from the dead insects;
- Sorting the eggs from the adults and sorting the eggs from the substrate;
- Sorting the nymphs from the larvae;
- Cleaning a rearing container;
- Filling a rearing container with insects;
- Taking a rearing unit from rearing and sending it to another process;
- Introducing a new rearing unit;
- Throwing away the contents of a rearing container.

The rearing substrate corresponds to the medium added to the containers, which promotes the life and development of the insects or larvae or nymphs. The substrate used can be in the form of a dry solid, a damp solid, or can be liquid.

In the example shown, the island E corresponds to a station suitable for carrying out a sequence of feeding the insects (or larvae, or nymphs, etc.). The feeding island E is equipped with a feeding device E1.

According to different variants of the invention, the feeding either requires, or does not require, the containers forming the basic rearing units to be depalletized and degrouped, i.e. the aforementioned operation denoted "partially or totally degrouping the rearing containers from a basic rearing unit". Thus, the depalletization can consist of separating each container of a basic unit from one another, in order to obtain a set of individual containers, or separating one basic unit into groups of containers (typically four to six containers).

The depalletization and the palletization, in the feeding island E as well as at the level of the first and second logistical zones B1, C1, can for example be carried out using a polyarticulated handling robot, for example a six-axis robot or a seven-axis robot. Such a robot can allow more generally handling of the rearing containers at speeds, accelerations, and maintaining a position, compatible with insect rearing.

The feeding device E1, whether or not the containers of the basic unit are, or are not, degrouped, ensures a substantially uniform distribution of food in the containers.

The feeding island E can optionally allow water to be provided in the rearing containers. This provision of water can be carried out according to various alternative or additional modes: by periodically filling a dedicated tank of the containers, by fogging, by provision of water-rich food or water-enriched food.

Thus a feeding sequence can comprise the following sequence of operations:
- Removing a basic rearing unit (from the first zone Z1) from storage;
- Partially or totally degrouping the rearing containers from a basic rearing unit (optional operation according to the variant of the invention in question);
- Separating the droppings from the containers (optional operation in this sequence);
- Depositing rearing substrate in the rearing containers;
- Providing water in the rearing containers (optional operation according to the variant of the invention in question);

Grouping together the rearing containers as a basic rearing unit (optional operation according to the variant of the invention in question);

Storing the basic rearing unit in a controlled environment (in the first zone Z1).

In the example shown, the island D is specialized in washing the rearing containers. It can in particular comprise one or more washing tunnels D1 suitable for washing rearing compartments and/or pallets.

In the example shown here, the washing island D is configured in order to allow, when necessary, the supply of clean containers to islands B and C.

An example washing sequence can implement the following sequence of operations (some operations may be reversed):

Removing from storage a basic rearing unit (from the first zone Z1);
Partially or totally degrouping the rearing containers from a basic rearing unit;
Emptying the rearing containers;
Separating the droppings and the substrate from the live larvae;
Cleaning the rearing containers (this operation comprising the washing and drying of the containers);
Storing the containers in a dedicated zone before re-use, or sending the containers for re-use;

In the example shown, islands B and C correspond to a first modular island B and a second modular island C. The islands B and C are called modular in that they comprise a certain number of items of equipment that can be easily interchanged or upgraded so that they can easily be specialized for various rearing sequences and/or operations. In the configuration shown, the modular islands B, C each comprise a logistics zone B1, C1 equipped for example with a polyarticulated handling robot, for example a six-axis or seven-axis robot. The robot with which these zones are equipped allows rearing containers to be degrouped (operation of "partially or totally degrouping the rearing containers from a basic rearing unit") when this is necessary for the subsequent carrying out of a rearing operation, and optionally the grouping together and palletization of the containers into basic units (operation of "grouping together the rearing containers into a basic rearing unit") after carrying out a rearing operation at the level of the corresponding island. The handling robot can also, if applicable, empty the containers, for example into hoppers feeding the machines of the island.

The island is also configured in order to allow other operations to be carried out on basic units or containers. The island thus comprises one or more stations, or one or more machines, to which the basic units, the containers, or the contents of the containers must be sent. This function can be partially ensured by the six-axis robot, for example for placing a container on a conveyor bringing the basic unit or the container to a given station.

In the example shown, the first modular island B comprises a first separator B2, configured for separating live larvae, dead larvae and droppings.

The first modular island B also comprises in particular a second separator B3, configured for the grading of the (live) larvae, i.e. the segregation of the larvae as a function of their size or their weight. Numerous sorting machines can be envisaged. A large number of items of separation equipment is known, allowing the insects to be sorted according to:

their size;
their physiological stage;
whether they are dead or alive; and/or separating the fine waste (droppings, substrate that has not been consumed, molds, etc.) from the insects.

Among these items of equipment, there may be mentioned for example separation tables, optical sorting systems, vibrating sieves, etc.

An item of equipment can be configured and parametered in order to carry out different sorting operations.

The number of items of separation equipment utilized can be adapted to the needs of the rearing in question.

Figure 4:
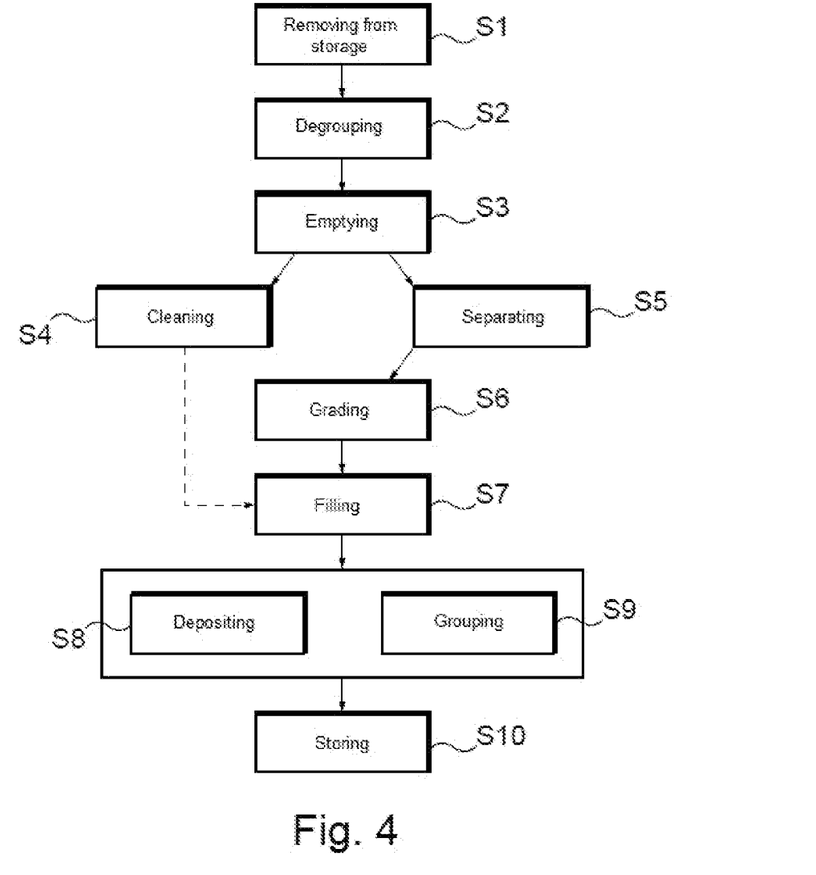
FIG. 4 shows, in the form of a flow chart, a particular operating sequence for grading larvae, that can be implemented for the synchronization of the insects.

The second separator B3 can thus be used typically in a grading sequence of the larvae according to their size, which can comprise the following sequence of operations (some operations may be reversed or carried out in parallel), and which is shown diagrammatically in FIG. 4:

Removing (S1) a basic rearing unit (from the first zone Z1) from storage;
Partially or totally degrouping (S2) the rearing containers from a basic rearing unit;
Emptying (S3) the rearing containers;
Cleaning (S4) the rearing containers (in parallel with the following separation and grading operations);
Separating (S5) the droppings and the live larvae;
Grading (S6) the larvae according to their size;
Filling (S7) the rearing containers with the insects (i.e. in this case the live larvae, and according to the preceding grading);
Depositing (S8) rearing substrate in the rearing containers;
Grouping together (S9) the rearing containers into a basic rearing unit;
Providing water in a rearing container (optional operation according to the variant of the invention in question);
Storing (S10) the basic rearing units in a controlled environment (in the first zone Z1).

This sequence can typically be used for the synchronization of the insects at the larval stage. As clearly shown in FIG. 4, the steps of "depositing (S8) substrate" and "grouping together (S9) the containers" can be reversed, according to the variant of the process in question. Similarly, the clean containers used in the step of "filling (S7) containers" are not necessarily the same containers as those emptied in the step of "emptying (S3)". The steps of "separating (S5)" and "grading (S6)" on the one hand and "cleaning (S4)" on the other hand can be conducted in parallel or sequentially, as they are independent.

In the example shown, the second modular island C comprises a separator (for example a screen C2), configured for the separation between adult insects, eggs, and rearing substrate (medium added to the containers suitable for the life of the insects or larvae or nymphs). This can be in particular a series of sieves, the successive sieves separating the stages being increasingly fine in order to carry out the aforementioned separation. However, other types of machines can be used, as previously mentioned. The second modular island C also comprises in the example shown a third air sifter C3 (or other separation tool), configured for the separation between adult insects, larvae and nymphs.

The second modular island C also comprises a fourth air sifter C4 (or other separation tool), configured for the separation between live adult insects and dead insects. This fourth air sifter C4 (or other separation tool) can thus be used typically in a sequence for sorting the live adults from the dead, comprising the following sequence of operations (some operations may be reversed):

Removing a basic rearing unit (of the first zone Z1) from storage;

Partially or totally degrouping the rearing containers from a basic rearing unit;

Emptying the rearing containers;

Sorting the live adults from the dead adults;

Filling the rearing containers with the insects (i.e. in this case the live larvae, according to the preceding grading);

Grouping together the rearing containers into a basic rearing unit;

Depositing rearing substrate in a rearing container;

Providing water in a rearing container (optional operation according to the variant of the invention in question);

Storing the basic rearing units in a controlled environment (in the first zone Z1).

According to the variant of the process in question, the steps of "depositing substrate" and "grouping together the containers" can in particular be reversed.

In the example shown here, the second modular island C also comprises a fifth air sifter C5 configured for the separation between larvae and nymphs. This separator is optional.

The organization of the farm, and in particular of the second zone Z2 given here by way of example, allows the implementation of all of the periodic operations of insect rearing, from the egg up to obtaining adult insects having the desired level of growth. Many other modes of organization are possible, utilizing a larger or smaller number of islands or stations.

In particular, in order to optimize the rearing yield, it is convenient to rear the insects (eggs, larvae, nymphs, adults, etc.) with an optimized density in the containers. The density of insects can typically correspond to a weight of insects by volume or by surface area of the container or a number of insects by volume or by surface area of the container.

An optimized density can typically correspond to the density of insects for which a storage phase ends with a density considered maximal guaranteeing the good health of the insects in the basic unit or the containers (an optional safety margin being applied if necessary). This can be obtained by the implementation of a sequence called concentration/dilution sequence. In a sequence called concentration/dilution of the insects, the density of insects in each container of a rearing unit is brought to a target density by the addition of insects, the removal of insects, or the distribution of the insects in the containers. The target density corresponds to a desired predetermined density at the start of the subsequent storage phase.

In particular, the target density can correspond to a density for which it is estimated that the desired time interval separating the current concentration/dilution sequence from a following concentration/dilution sequence will end with a density considered maximal guaranteeing good health of the insects in the containers. A simple way to define a target density is to associate therewith a predefined percentage of the insect density considered maximal guaranteeing good health of the insects in the containers.

More simply, the target density can correspond to one half of the density reached at the end of the preceding growth phase, which leads for example to simply equally distributing the insects from each container into two containers. Similarly, the insects from each container can also be distributed into three, four or more containers. Other distributions are possible, for example the insects from two containers being distributed equally into three containers.

Figure 5:
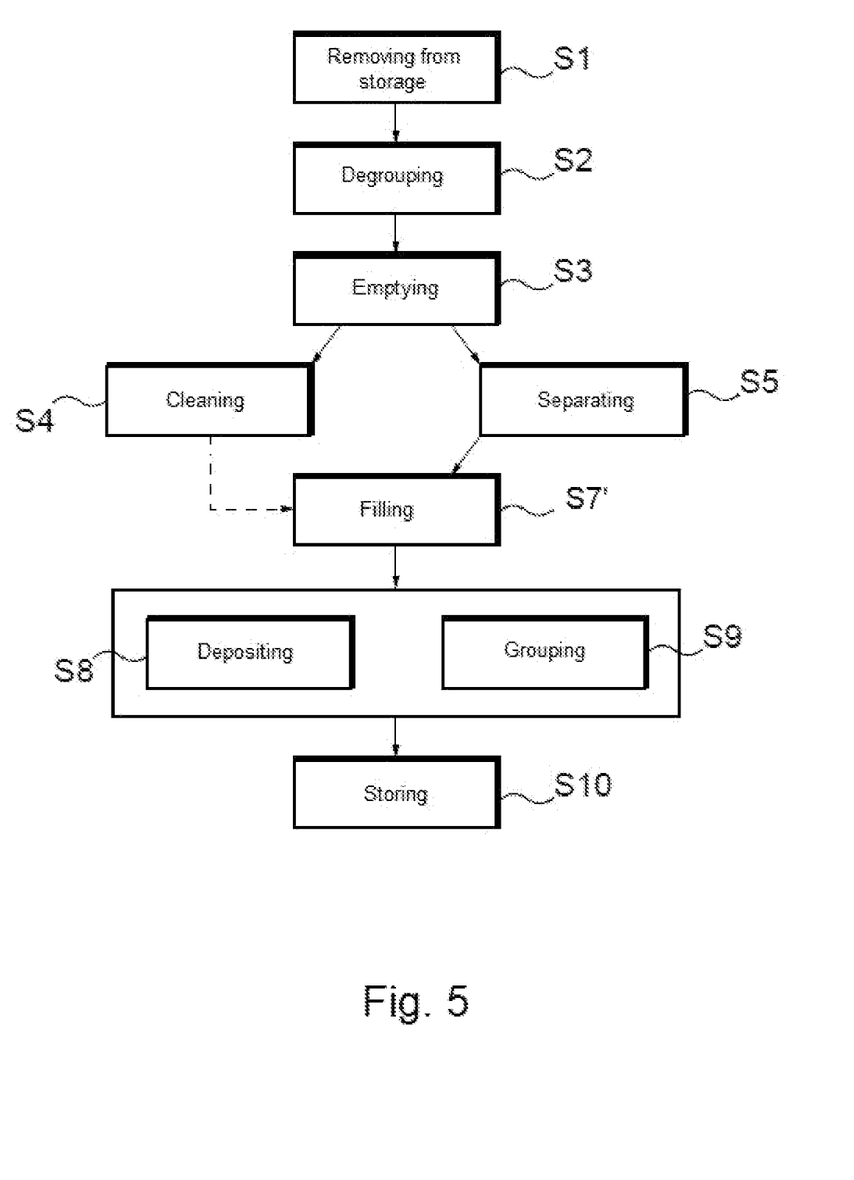
FIG. 5 shows, in the form of a flow chart, a particular operating sequence called concentration/dilution sequence.

In particular, the concentration/dilution operating sequence, shown in FIG. 5, can comprise the sequence of the following operations:

Removing (S1) a basic rearing unit (from the first zone Z1) from storage; then

Totally degrouping (S2) the rearing containers from the basic rearing unit; then Emptying (S3) the rearing containers; then Cleaning (S4) the containers; and Separating (S5) the droppings and the live larvae; then Filling (S7') rearing containers with insects, to the target density; then Depositing (S8) rearing substrate and/or providing water; and Grouping together (S9) the rearing containers into a basic rearing unit; then Storing (S10) the basic rearing units in a controlled environment;

As clearly shown in FIG. 5, the steps of "depositing (S8) substrate" and "grouping together (S9) the containers" can be reversed, according to the variant of the process in question. Similarly, the clean containers used in the step of "filling (S7') containers" are not necessarily the same containers as those emptied in the step of "emptying (S3)". The steps of "separating (S5)" and "cleaning (S4)" can be conducted in parallel or sequentially, as they are independent.

An insect rearing can implement for example three parallel processes, namely: a process called production process, which relates to the development of eggs or juveniles up to a larval stage of a given maturity that can correspond to the final product of the rearing before any transformation, a process called reproduction process, which relates to the development of eggs or juveniles up to the stage of young adults, and a process called egg-laying process, which relates to the production of eggs or juveniles by adult insects.

Figure 6:
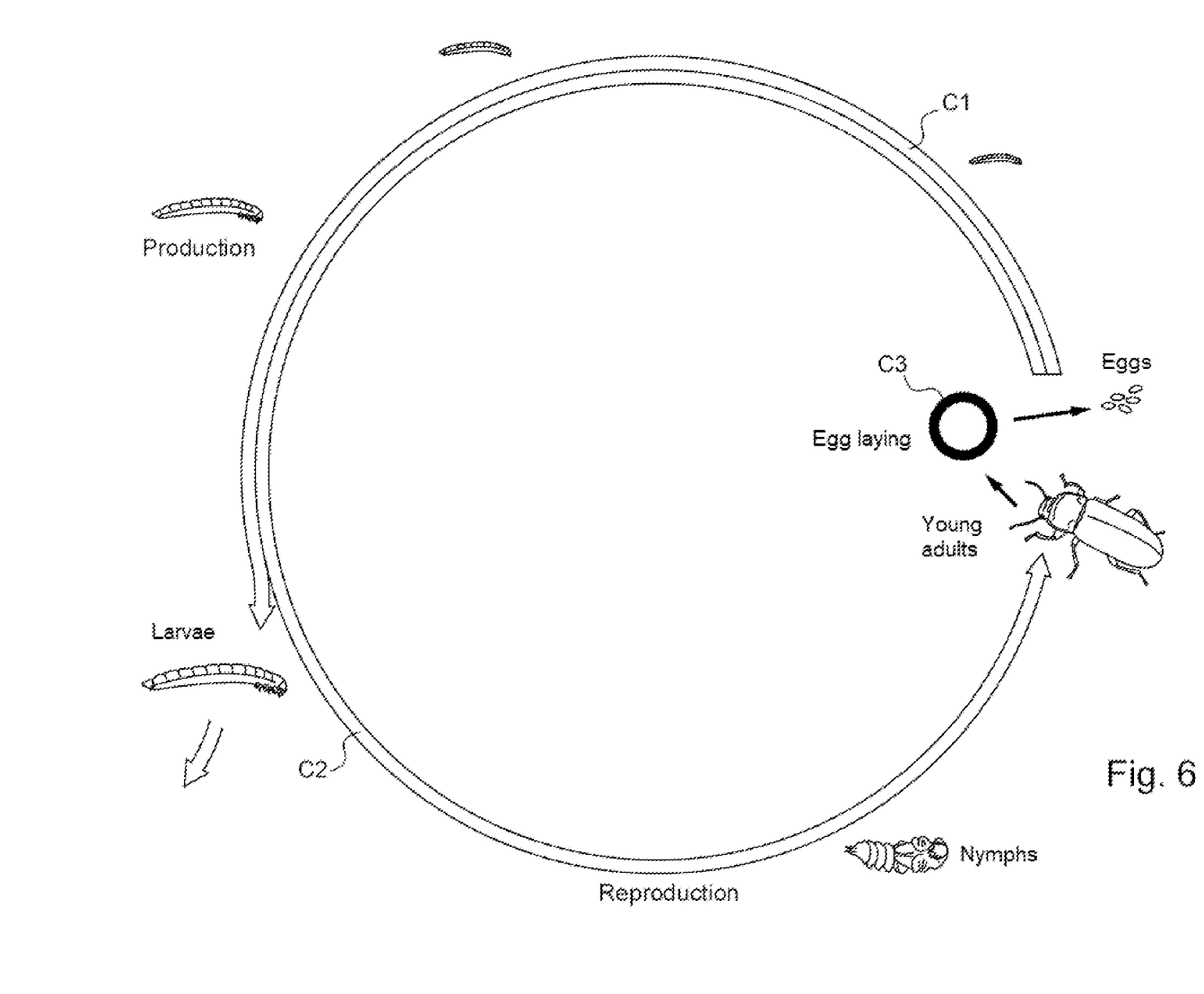
FIG. 6 shows diagrammatically three processes which can coexist in insect rearing, in the particular example of the rearing of yellow mealworms.

The three aforementioned processes and their chronological continuity are shown diagrammatically in FIG. 6, in the particular example of rearing yellow mealworms under optimized environmental conditions. The three processes are illustrated cyclically, each of the processes being capable of feeding another or being fed by another.

An arc of circle C1 corresponds to the process called production process, which relates to the development of eggs or juveniles up to a larval stage of a given maturity that can correspond to the final product of the rearing before any transformation. This process can typically last for approximately 6 to 14 weeks, in the example shown.

A full circle C2 corresponds to the process called reproduction process, which relates to the development of eggs or juveniles up to the stage of young adults, and which relates in particular to the rearing of insects intended to become reproductive and to be incorporated into an egg laying process. This process can typically last for approximately 10 to 24 weeks, in the example shown.

A ring C3 represents the process called egg-laying process, which relates to the production of eggs or juveniles by adult insects. An egg laying cycle of an adult lasts for approximately one week. The adults can repeat several cycles of egg laying.

As shown, the adults intended for egg laying can originate from the process called reproduction process (the egg laying process thus completes the circle for a part of the adults obtained originating from said reproduction process). The eggs (or juveniles) obtained originating from the egg laying process are directed either to the entry of a production process, or to a reproduction process.

For each process, different rearing sequences or operations are implemented at predefined intervals (corresponding to growth phases), in order to optimize the rearing in terms of growth, yield, and insect welfare.

Typically, the production process can, in the example shown, comprise carrying out two sequences quite frequently, namely the feeding sequences (for example once or twice a week) and cleaning the compartments (for example, once every two weeks). Examples of successive operations constituting these sequences have been given previously. The production process can also comprise, for example once or twice in the process, the synchronization of the insects by implementation of a grading sequence of the larvae for example by using the succession of operations described previously for this sequence. The production process can also comprise, for example once or twice in the process, a concentration/dilution sequence of the insects according to the succession of operations described previously for this sequence.

The start of the reproduction process has the same rearing sequences as the production process. The reproduction process advantageously comprises, once during said process, a concentration/dilution sequence leading to an extreme dilution, during which the target density is far below the initial density of insects. In fact this involves, during this extreme dilution and within the context of rearing yellow mealworms or other Coleoptera, redistribution from the containers comprising a volume of insects (larvae, etc.) into containers so as to obtain no more than a single layer of insects on the base of the container.

The reproduction process also comprises sequences or operations that are repeated typically once a week, at least during a part of the process (by time). Thus the following operations can be conducted quite frequently:

Separating the larvae, the nymphs and the adults;
Separating the eggs from the adults;
Separating the dead insects (nymphs or adults) from the live ones;
Separating the diseased individuals from the healthy individuals;
Selecting insects intended for the egg laying process.

The egg laying process itself is the continuation of the reproduction process. In fact, the adult insects selected at the end of the reproduction process are introduced into the egg laying containers, with the older insects already active in terms of egg laying, and after removing the dead adults from the egg laying containers. This is therefore a circular process. The cycle can be of the order of a week, i.e. each week the operations of removing the dead and re-stocking will be carried out. Moreover, periodically, the egg laying process can comprise a sequence intended to concentrate the eggs or the larvae (concentration/dilution sequence with a target density greater than the initial density).

The egg laying process, inasmuch as it does not comprise a synchronization sequence, is ancillary to a process according to the invention. For example, it can complete in particular a reproduction process according to a variant of the invention, itself supporting a production process according to a variant of the invention.

Various operations called support operations can also be conducted during a rearing process. These can be for example:

monitoring the good health of the insects by means of sensors (in the containers, or in the storage zone) or by taking an image at the time of carrying out rearing sequences or operations;
disinfecting the containers;
carrying out sampling of the production batches, in order to closely analyze the content of the containers (microbiological analysis, protein content of the insects, etc.)
carrying out data collection, in particular with a view to guaranteeing the traceability of the process, for example carrying out weighing of the containers throughout the rearing process, and feeding a database on each of the batches for example by indicating therein what sequence or operation was carried out and at what time, the parameters used for this sequence (for example what quantity of feed was provided);
guaranteeing a certain genetic mixing by periodically incorporating new strains of insects into the rearing.

The sequencing of the rearing operations, although simplified in the invention by the fact that the basic units contain insects at the same stage of development or of the same maturity, requires a spatial and time-based organization and monitoring of the basic units, or even the containers. Such monitoring can be carried out by a computerized device making it possible to monitor carrying out the different rearing operations during said rearing. In particular, the rearing process follows a succession of steps, i.e. typically a precise ordering of the rearing sequences and operations carried out following a predefined calendar, which can optionally be corrected during rearing, depending on the development of the insects' growth (egg, egg sacs, larvae, pupae or nymphs).

In order to be able to monitor the progress of the rearing process efficiently, the farm is advantageously provided with a system for monitoring the basic units, and/or certain containers, and/or each of the containers.

The system for monitoring the basic units, and/or certain containers, and/or each of the containers can in particular utilize RFID (radio frequency identification often known as radio-identification) technology. An RFID tag can if appropriate be associated with the basic units, or containers, with reader systems allowing their identification being arranged in the farm, typically at the level of the interface between the first zone and the second zone (in order to manage the position of the basic unit in the racks of the first zone Z1), and at the entry to and/or the exit from the different stations at which the rearing sequences or operations are carried out. The RFID system implemented can also allow the instant identification of the set of compartments constituting a pallet. This RFID system is advantageously linked to a database that allows the traceability of each of the containers to be guaranteed. The traceability relates to the entire rearing process, from the raw materials used for rearing, to the insects (feed, substrate, etc.) up to killing and the finished products.

Other means for identification and collection of corresponding data can be used successfully, for example wireless communication, for example according to a WiFi, Bluetooth or Zigbee (registered trade marks) protocol. A low-throughput system utilizing low-frequency radio waves can also be successfully implemented.

Thus, the farm is also advantageously equipped with a computerized system for monitoring production, associated with monitoring means of the RFID type or another type. The production, and in particular the rearing process according to the invention, can thus be driven in an automated manner, the system being able typically to associate certain sequences or operations with certain basic rearing units, and at the end of a growth phase, to control the collection of a given basic rearing unit in the first storage zone, the implementation of the desired sequence, and the return to a given position of the basic unit.

Typically, since the stage of development and growth of the insects (eggs, larvae, nymphs, adult insects) in one and the same basic rearing unit is theoretically identical, the monitoring of the basic units is generally sufficient for driving the automated devices of the farm.

Monitoring of certain particular containers can allow for example the periodic withdrawal and sampling of these particular containers to carry out checks or assessments.

Finally, individual monitoring of the containers, requiring the identification of each of said containers, allows full and individualized monitoring of the rearing process. It makes it possible in particular to reconstitute basic units when required during the rearing with containers originating from other basic units or with new containers.

A rearing process according to the invention can be used for rearing many species of insects, by means of minor adaptations, typically in defining and planning the rearing sequences.

Generally, a single species is reared in one farm. Several species can also be reared, preferably in separate parts of the farm. Within the context of a farm suitable for simultaneously rearing several species of insects, certain synergies can be exploited. Typically, certain larvae, live or dead insects of one species, or the by-products of production and rearing, can be used to feed another species.

The product(s) of interest ultimately obtained, after reuse of the rearing products, are obtained from insects. As mentioned previously, by "insects" is meant insects regardless of the stage of development, such as an adult or larval stage or a nymph stage. Preferably, the insects utilized in the process according to the invention are edible.

More particularly, the insects can be selected from the group constituted by Coleoptera, Diptera, Lepidoptera, Isoptera, Orthoptera, Hymenoptera, Blattoptera, Hemiptera, Heteroptera, Ephemeroptera and Mecoptera, preferably, from Coleoptera, Diptera, Orthoptera and Lepidoptera.

Preferentially, the insects are selected from the group constituted by *Tenebrio molitor* (or yellow mealworms), *Hermetia illucens*, *Rhynchophorus ferrugineus*, *Galleria mellonella*, *Alphitobius diaperinus*, *Zophobas morio*, *Blattera fusca*, *Musca domestica*, *Chrysomya megacephala*, *Locusta migratoria*, *Schistocerca gregaria*, *Acheta domestica* and *Samia ricini*.

Favourable conditions, in particular in the first zone where the insects are stored during their growth, can allow rapid development and reproduction of the insects. For example, the full developmental cycle of the yellow mealworm, from the egg to the full grown adult, can take from two to three months at a temperature of 15° C. to 35° C., while it can take a year in the natural environment.

A process according to the invention thus allows large-scale insect rearing with minimal costs by virtue of its high optimization (linked for example to the synchronization and/or concentration/dilution sequences) and a possible high level of automation.

The growth of the insects takes place in a zone with a controlled, or even computer-driven, atmosphere (temperature, hygrometry, etc.), in order to offer optimal growth conditions for the insects at all stages from the egg to the adult. By the synchronization and optional optimization of the density of the insects in the containers, the process can have a very high production yield. By way of example, it is estimated that by using racks 12 metres in height in the first zone Z1, a farm according to the invention could allow the production of 10,000 tonnes annually of protein flour per hectare in use, while a soya crop allows the production thereof of one to five tonnes per hectare annually, and rearing pigs or chickens in batteries allows the production of an equivalent of a few tens of tonnes per hectare annually.

The method proposed in the invention, based on a sequential ordering in two separate zones of single operations alternating with "passive" periods of storage for the growth of the insects is suitable for the production of insects on an industrial scale. By way of example, a farm of a modest size according to the invention could produce a minimum of one tonne of larvae daily, having a zone suitable for the storage of fifty tonnes of insects (eggs, larvae, nymphs and adults) distributed over 500 pallets. The rearing operations in this case require the movement of approximately 100 to 200 pallets daily. A large-scale industrial operation, responding to the needs of the markets in animal feedstuffs for example, could thus typically lead to the adoption of values fifty to one hundred times greater than those mentioned previously, depending on the markets envisaged.

Finally, rearing in accordance with a process according to the invention can be carried out with means allowing rigorous control and monitoring, limiting the health risks in the farm.

The invention claimed is:

1. A process for rearing insects comprising:
   conducting at least two growth phases and at least two operating sequences on insects,
   wherein said sequences and phases alternate and wherein at least one of said operating sequences is a synchronization sequence comprising the steps of:
   (a) sorting a batch of insects based upon one or more categories of size;
   (b) distributing the insects of each category into one or more container(s); and
   (c) grouping together identical containers containing insects of the same category into one or more basic rearing unit(s) ("BU(s)"), and
   comprising the following operating sequences:
   collecting eggs from the rearing containers containing insects intended for egg-laying, and
   concentrating eggs in rearing containers.

2. The rearing process according to claim 1, in which the synchronization sequence is conducted several times on each insect during said process.

3. The rearing process according to claim 1, wherein at least one of said operating sequences is a concentration/dilution sequence of the insects wherein the density of insects in each container of a rearing unit is brought to a target density by: (a) the addition of insects, (b) the removal of insects, or (c) the distribution of the insects in containers, wherein said target density corresponds to a desired predetermined density at the start of the subsequent storage phase.

4. The rearing process according to claim 3, wherein the target density corresponds to the density for which it is estimated that, taking account of the expected growth of the insects during the subsequent storage phase, the desired time interval separating the current concentration/dilution sequence from a following concentration/dilution sequence will end with a density considered maximal guaranteeing the good health of the insects in the containers.

5. The rearing process according to claim 3, wherein the target density is defined by a ratio of the density in the containers before the concentration/dilution sequence.

6. The rearing process according to claim 3, wherein a density of insects is either:
- a weight of insects by volume or by surface area of the container; or
- a number of insects by volume or by surface area of the container.

7. The rearing process according to claim 1, wherein said process combines:
- a production process, for insect rearing from the egg or from the juvenile stage up to the larval stage with a predefined maturity; and
- a reproduction process, for insect rearing from the egg or from the juvenile stage up to the young adult stage, associated with a process called egg-laying process, relating to the production of eggs or juveniles by adult insects.

8. The rearing process according to claim 1, comprising, between each growth phase, a step of automated transport of the BU(s) containing the insects that are to be the subject of at least one operating sequence, from a storage zone in which said growth phase takes place, to an operating zone comprising work stations suitable for rearing operations of the operating sequence.

9. The rearing process according to claim 1, comprising an operating sequence for the withdrawal of adult insects intended for egg laying.

10. The rearing process according to claim 1, wherein at least one of said operating sequences comprises the ordered succession of several operations among the following operations:
- storing a basic rearing unit in a controlled environment;
- removing a basic rearing unit from storage;
- partially or totally degrouping the rearing containers from a basic rearing unit;
- grouping together rearing containers into a basic rearing unit;
- depositing rearing substrate in a rearing container;
- providing water in a rearing container;
- emptying a rearing container;
- identifying the individuals having symptoms of disease in order to remove them from the container;
- separating the fine waste, comprising the droppings, the remains of the substrate, and the molts, from the insects;
- separating the mature live larvae and the substrate that has not been consumed;
- separating the dead larvae from the live larvae;
- grading the larvae according to their size;
- sorting the adult insects from the larvae and the nymphs;
- sorting the live insects from the dead insects;
- sorting the eggs from the adults and sorting the eggs from the substrate;
- sorting the nymphs from the larvae;
- cleaning a rearing container;
- filling a rearing container with insects;
- taking a rearing unit from rearing and sending it to another process;
- introducing a new rearing unit; and
- throwing away the contents of a rearing container.

11. A process for rearing insects comprising: conducting at least one growth phase and at least one operating sequence on insects, wherein said sequence(s) and phase(s) alternate, and wherein at least one of said operating sequences is a synchronization sequence carried out at the larval stage by implementation of a grading sequence of the larvae comprising the following operations:
- removing a basic rearing unit from storage;
- partially or totally degrouping the rearing containers from the basic rearing unit;
- emptying the rearing containers;
- cleaning the rearing containers;
- separating the droppings and the live larvae;
- grading the larvae according to their size;
- filling the clean rearing containers with the live larvae;
- depositing rearing substrate in the rearing containers;
- grouping together the rearing containers into a basic rearing unit; and
- storing the basic rearing unit in a controlled environment.

12. The rearing process according to claim 11, further providing water to the insects in the rearing containers.

13. A process for rearing insects comprising:
- conducting at least one growth phase and at least one operating sequence on insects, wherein said sequence(s) and phase(s) alternate,
- wherein at least one of said operating sequences is a concentration/dilution sequence of the insects wherein the density of insects in each container of a rearing unit is brought to a target density by: (a) the addition of insects, (b) the removal of insects, or (c) the distribution of the insects in containers, wherein said target density corresponds to a desired predetermined density at the start of the subsequent storage phase, and
- wherein said concentration/dilution sequence comprises the following operations:
  - removing a basic rearing unit from storage;
  - totally degrouping the rearing containers from the basic rearing unit;
  - emptying the rearing containers;
  - cleaning the rearing containers;
  - separating the droppings and the live larvae;
  - filling the clean rearing containers with insects to the desired density;
  - depositing rearing substrate in the rearing containers;
  - grouping together the rearing containers into a basic rearing unit; and
  - storing the basic rearing unit in a controlled environment.

14. The rearing process according to claim 13, further comprising providing water to the insects in the rearing containers.

15. The rearing process according to claim 13, wherein at least one of said operating sequences comprises:
- collecting juvenile insects from the rearing containers containing insects intended for egg laying, and
- concentrating juveniles in rearing containers.

16. A process for rearing insects comprising:
- conducting at least two growth phases and at least two operating sequences on insects,
- wherein said sequences and phases alternate and wherein at least one of said operating sequences is a synchronization sequence comprising the steps of:
  - (a) sorting a batch of insects based upon one or more categories of size;
  - (b) distributing the insects of each category into one or more container(s); and
  - (c) grouping together identical containers containing insects of the same category into one or more basic rearing unit(s) ("BU(s)"), and
- wherein at least one of said operating sequences comprises:
  - collecting juveniles from the rearing containers containing insects intended for egg-laying, and
  - concentrating juveniles in rearing containers.

17. The rearing process according to claim 16, in which the synchronization sequence is conducted several times on each insect during said process.

18. The rearing process according to claim 16, wherein at least one of said operating sequences is a concentration/dilution sequence of the insects wherein the density of insects in each container of a rearing unit is brought to a target density by: (a) the addition of insects, (b) the removal of insects, or (c) the distribution of the insects in containers, wherein said target density corresponds to a desired predetermined density at the start of the subsequent storage phase.

19. The rearing process according to claim 18, wherein the target density corresponds to the density for which it is estimated that, taking account of the expected growth of the insects during the subsequent storage phase, the desired time interval separating the current concentration/dilution sequence from a following concentration/dilution sequence will end with a density considered maximal guaranteeing the good health of the insects in the containers.

20. The rearing process according to claim 18, wherein the target density is defined by a ratio of the density in the containers before the concentration/dilution sequence.

21. The rearing process according to claim 18, wherein a density of insects is either:
   a weight of insects by volume or by surface area of the container; or
   a number of insects by volume or by surface area of the container.

22. The rearing process according to claim 16, wherein said process combines:
   a production process, for insect rearing from the egg or from the juvenile stage up to the larval stage with a predefined maturity; and
   a reproduction process, for insect rearing from the egg or from the juvenile stage up to the young adult stage, associated with a process called egg-laying process, relating to the production of eggs or juveniles by adult insects.

23. The rearing process according to claim 16, comprising, between each growth phase, a step of automated transport of the BU(s) containing the insects that are to be the subject of at least one operating sequence, from a storage zone in which said growth phase takes place, to an operating zone comprising work stations suitable for rearing operations of the operating sequence.

24. The rearing process according to claim 16, comprising an operating sequence for the withdrawal of adult insects intended for egg laying.

25. The rearing process according to claim 16, wherein at least one of said operating sequences comprises the ordered succession of several operations among the following operations:
   storing a basic rearing unit in a controlled environment;
   removing a basic rearing unit from storage;
   partially or totally degrouping the rearing containers from a basic rearing unit;
   grouping together rearing containers into a basic rearing unit;
   depositing rearing substrate in a rearing container;
   providing water in a rearing container;
   emptying a rearing container;
   identifying the individuals having symptoms of disease in order to remove them from the container;
   separating the fine waste, comprising the droppings, the remains of the substrate, and the molts, from the insects;
   separating the mature live larvae and the substrate that has not been consumed;
   separating the dead larvae from the live larvae;
   grading the larvae according to their size;
   sorting the adult insects from the larvae and the nymphs;
   sorting the live insects from the dead insects;
   sorting the eggs from the adults and sorting the eggs from the substrate;
   sorting the nymphs from the larvae;
   cleaning a rearing container;
   filling a rearing container with insects;
   taking a rearing unit from rearing and sending it to another process;
   introducing a new rearing unit; and
   throwing away the contents of a rearing container.

* * * * *